United States Patent
Preil et al.

(10) Patent No.: US 7,853,920 B2
(45) Date of Patent: Dec. 14, 2010

(54) METHOD FOR DETECTING, SAMPLING, ANALYZING, AND CORRECTING MARGINAL PATTERNS IN INTEGRATED CIRCUIT MANUFACTURING

(75) Inventors: Moshe E. Preil, Sunnyvale, CA (US); Jun Ye, Palo Alto, CA (US); James N. Wiley, Menlo Park, CA (US); Shauh-Teh Juang, Saratoga, CA (US); Michael J. Gassner, San Jose, CA (US)

(73) Assignee: ASML Netherlands B.V., Veldhoven (NL)

( * ) Notice: Subject to any disclaimer, the term of this patent is extended or adjusted under 35 U.S.C. 154(b) by 604 days.

(21) Appl. No.: 11/437,594

(22) Filed: May 19, 2006

(65) Prior Publication Data
US 2006/0273266 A1    Dec. 7, 2006

Related U.S. Application Data

(60) Provisional application No. 60/686,625, filed on Jun. 3, 2005.

(51) Int. Cl.
*G06F 17/50*    (2006.01)
*G06K 9/00*    (2006.01)

(52) U.S. Cl. .................. 716/21; 716/19; 382/149; 430/30

(58) Field of Classification Search ............. 716/19–21; 382/149
See application file for complete search history.

(56) References Cited

U.S. PATENT DOCUMENTS

| | | | |
|---|---|---|---|
| 6,757,645 B2 * | 6/2004 | Chang et al. | 703/13 |
| 6,803,554 B2 | 10/2004 | Ye et al. | |
| 6,806,456 B1 | 10/2004 | Ye et al. | |
| 6,828,542 B2 | 12/2004 | Ye et al. | |
| 7,003,758 B2 | 2/2006 | Ye et al. | |
| 7,027,143 B1 * | 4/2006 | Stokowski et al. | 356/237.2 |
| 7,107,571 B2 * | 9/2006 | Chang et al. | 716/19 |
| 7,123,356 B1 * | 10/2006 | Stokowski et al. | 356/237.2 |
| 7,135,344 B2 * | 11/2006 | Nehmadi et al. | 438/14 |
| 2002/0019729 A1 * | 2/2002 | Chang et al. | 703/6 |
| 2002/0035461 A1 * | 3/2002 | Chang et al. | 703/13 |
| 2005/0010890 A1 * | 1/2005 | Nehmadi et al. | 716/19 |
| 2006/0120599 A1 * | 6/2006 | Steinberg et al. | 382/167 |
| 2006/0123380 A1 * | 6/2006 | Ikeuchi | 716/21 |
| 2006/0291714 A1 * | 12/2006 | Wu et al. | 382/149 |
| 2007/0288219 A1 * | 12/2007 | Zafar et al. | 703/14 |
| 2008/0163140 A1 * | 7/2008 | Fouquet et al. | 716/4 |

* cited by examiner

*Primary Examiner*—Vuthe Siek
*Assistant Examiner*—Patrick Sandoval
(74) *Attorney, Agent, or Firm*—Pillsbury Winthrop Shaw Pittman LLP

(57) ABSTRACT

One embodiment of a method for detecting, sampling, analyzing, and correcting hot spots in an integrated circuit design allows the identification of the weakest patterns within each design layer, the accurate determination of the impact of process drifts upon the patterning performance of the real mask in a real scanner, and the optimum process correction, process monitoring, and RET improvements to optimize integrated circuit device performance and yield. The combination of high speed simulation coupled with massive data collection capability on actual aerial images and/or resist images at the specific patterns of interest provides a complete methodology for optimum RET implementation and process monitoring.

28 Claims, 3 Drawing Sheets

METHOD FOR DETECTING, SAMPLING, ANALYZING, AND CORRECTING MARGINAL PATTERNS IN INTEGRATED CIRCUIT MANUFACTURING

CROSS-REFERENCE TO RELATED APPLICATION

This application claims the benefit of U.S. Provisional Patent Application No. 60/686,625, filed Jun. 3, 2005 entitled "Method for Detecting, Sampling, Analyzing and Correcting Marginal Patterns in Integrated Circuit Manufacturing." The subject matter of this related application is hereby incorporated by reference in its entirety.

FIELD OF THE INVENTION

This invention relates generally to optical lithography and more particularly to detecting, sampling, analyzing, and correcting marginal patterns in integrated circuit manufacturing.

BACKGROUND

The integrated circuit industry has, since its inception, maintained a remarkable growth rate by driving increased device functionality at lower cost. Leading edge devices today provide the computing power of computers that used to occupy entire rooms at a mere fraction of the cost. Many of today's low cost consumer devices include functionality that only a few years ago was unavailable at any cost, such as video cell phones, ultra-portable media players, and wireless or ultra wideband Internet devices. One of the primary enabling factors of this growth has been the ability of optical lithography processes to steadily decrease the smallest feature size that can be patterned as part of the integrated circuit pattern. This steady decline in feature size and cost while at the same time printing more features per circuit is commonly referred to as "Moore's Law" or the lithography "roadmap."

The lithography process involves creating a master image on a mask, or reticle, then replicating that pattern faithfully onto the device wafers. The more times a master pattern is successfully replicated within the design specifications, the lower the cost per finished device or "chip." Until recently, the mask pattern has been an exact duplicate of the desired pattern at the wafer level, with the exception that the mask level pattern may be several times larger than the wafer level pattern. This scale factor is then corrected during wafer exposure by the reduction ratio of the exposure tool. The mask pattern is typically formed by depositing and patterning a light absorbing material on a quartz or other transmissive substrate. The mask is then placed in an exposure tool known as a "stepper" or "scanner" where light of a specific exposure wavelength is directed through the mask onto the device wafers. The light is transmitted through the clear areas of the mask and attenuated by a desired amount, typically between 90% and 100%, in the areas that are covered by the absorbing layer. The light that passes through some regions of the mask may also be phase shifted by a desired phase angle, typically an integer fraction of 180 degrees. After being collected by the exposure tool, the resulting aerial image pattern is then focused onto the device wafers. A light sensitive material deposited on the wafer surface interacts with the light to form the desired pattern on the wafer, and the pattern is then transferred into the underlying layers on the wafer to form functional electrical circuits according to well known processes.

In recent years, the feature sizes being patterned have become significantly smaller than the wavelength of light used to transfer the pattern. This trend towards "sub-wavelength lithography" has resulted in increasing difficulty in maintaining adequate process margins in the lithography process. The aerial images created by the mask and exposure tool lose sharpness as the ratio of feature size to wavelength decreases. This ratio is quantified by the k1 factor, defined as the numerical aperture of the exposure tool times the minimum feature size divided by the wavelength. The lack of sharpness or image blur can be quantified by the slope of the aerial image at the threshold for image formation in the resist, a metric known as "edge slope," or "normalized image log slope," often abbreviated as "NILS." The smaller the NILS value, the more difficult it becomes to replicate the image faithfully onto a large number of device patterns with sufficient control to yield economically viable numbers of functional devices. The goal of successful "low k1 lithography" processes is to maintain the highest NILS possible despite the decreasing k1 value, thereby enabling the manufacturability of the resulting process.

New methods to increase the NILS in low k1 lithography have resulted in master patterns on the mask that are not exact copies of the final wafer level pattern. The mask pattern is often adjusted in terms of the size of the pattern as a function of pattern density or pitch. Other techniques involve the addition or subtraction of extra corners on the mask pattern ("serifs," "hammerheads," and other patterns), and even the addition of geometries that will not be replicated on the wafer. These non-printing "assist features" may include scattering bars, holes, rings, checkerboards, or "zebra stripes" to change the background light intensity ("gray scaling"), and other structures, which are well documented in the literature. All of these methods are often referred to collectively as "Optical Proximity Correction," or "OPC."

The mask may also be altered by the addition of phase shifting regions that may or may not be replicated on the wafer. A large variety of phase shifting techniques has been described at length in the literature including alternate aperture shifters, double expose masking processes, multiple phase transitions, and attenuating phase shifting masks. Masks formed by these methods are known as "Phase Shifting Masks," or "PSMs". All of these techniques to increase NILS at low k1, including OPC, PSM, and others, are referred to collectively as "Resolution Enhancement Technologies," or "RETs." The result of all of these RETs, which are often applied to the mask in various combinations, is that the final pattern formed at the wafer level is no longer a simple replicate of the mask level pattern. In fact, it is becoming impossible to look at the mask pattern and simply determine what the final wafer pattern is supposed to look like. This greatly increases the difficulty in verifying that the design data is correct before the mask is made and wafers exposed, as well as verifying that the RETs have been applied correctly and that the mask meets its target specifications.

Simulation based approaches have been developed to verify the correctness of the design and mask layout before the mask is fabricated. One such approach is described in U.S. Pat. No. 7,003,758, entitled "System and Method for Lithography Simulation," the subject matter of which is hereby incorporated by reference in its entirety and is referred to herein as "the simulation system." Even with the best possible RET implementation and verification, it is still not possible to optimize every feature of a design. Some structures will often not be properly corrected due to limitations of the technology, implementation errors, or conflicts with neighboring features. The simulation system can identify specific features of the design that will result in unacceptably small process windows or excessive critical dimension (CD) variation within the normally expected range of process conditions, such as focus and exposure variation. These defective regions must be corrected before the mask is made. However, even in the best designs, there will be structures or parts of structures that can not be optimally corrected. Although these weak areas can produce good chips, they may have marginally acceptable process windows and are likely to be the first locations within the device that will fail under varying process conditions, either due to variations of the wafer processing conditions, the mask processing conditions, or a combination of both. These weak areas are referred to herein as "hot spots."

A critical consideration for these hot spots is that while the structures in question may have marginally acceptable process windows if the mask is produced exactly as expected based on the design data, the process window may become unacceptably small if any variations in the mask-making process alter the patterned structure at the mask level in such a way as to reduce the available process window at the wafer level. The impact of hot spots on wafer level patterning, electrical behavior, and yield is thus a convolution of both the mask and wafer processes. While either process can be monitored separately, there does not currently exist a method and system to monitor the combined effect of both mask and wafer patterning processes to determine whether there are regions of the design with unacceptably reduced process windows.

In the prior art, the mask and wafer processes are monitored independently. Some metrology data is collected during the mask-making process, either at test locations in the scribeline or of representative structures in the device. Designer intent may be captured by measuring specific features in the device portion of the mask that are known to be critical to the electrical performance of the device. Given the limitations of the existing metrology tools, the number of points measured is limited to on the order of ten to a few hundred points, while the actual device contains hundreds of millions to billions of features. The full mask pattern can also be inspected for large defects, but is incapable of detecting critical dimension errors on the order of just a few nanometers unless the defects cover a large area. Specific features or parts of features that will result in unacceptable CD variation at the wafer level can not be detected by the current inspection tools.

Similarly, the wafer manufacturing process has previously been monitored for both CD variation and defects. A typical prior art monitoring system includes an image sensor unit having resolution-enhanced sensor elements and employs a method of aerial image acquisition. Such an image sensor unit and method of aerial image acquisition are described in U.S. Pat. No. 6,828,542, "System and Method for Lithography Process Monitoring and Control," the subject matter of which is hereby incorporated by reference in its entirety. Such an image sensor unit can be loaded onto the wafer stage of a lithographic projection system in place of a regular production semiconductor wafer and be repeatedly exposed with the projected image from a mask in the same way as a production wafer.

With reference to FIG. 1, in one embodiment of the invention disclosed in the U.S. Pat. No. 6,828,542, aerial image sensing system 100 includes lithographic equipment 10 (for example, a stepper), an image sensor unit 102, and a processor/controller 104, for example, a computer and/or data or image processing unit. Lithographic equipment 10 may include a mirror 12, a light source 14 to generate light 16 at a certain exposure wavelength, illumination optics 18, projection optics 20, and a chuck 22. Chuck 22 secures image sensor unit 102 in a fixed location using, for example, electrostatic or vacuum forces.

The optics of lithographic equipment 10 (for example, light source 14, illumination optics 18, and projection optics 20) interacts with a mask 26 to project an aerial image onto image sensor unit 102. Mask 26, in one embodiment of the invention disclosed in the U.S. Pat. No. 6,828,542, may be a product-type mask; that is, a mask used to form circuits during integrated circuit fabrication. As such, mask 26 contains the pattern to be replicated or printed on a wafer that ultimately contains the circuit design (or a portion thereof) of the integrated circuit. In this embodiment, image sensor unit 102 may be employed to evaluate the interaction between mask 26 and lithographic equipment 10 (whether production or non-production equipment) as well as characterize the performance of lithographic equipment 10.

In another embodiment of the invention disclosed in the U.S. Pat. No. 6,828,542, mask 26 may be a test mask that is used to inspect, characterize and/or evaluate the optical characteristics or response of lithographic equipment 10. In this regard, mask 26 may include a fixed, predetermined and/or known pattern against which the aerial image collected, sensed, sampled, measured and/or detected by image sensor unit 102 will be evaluated, measured, and/or compared. In this way, any errors or discrepancies in the aerial images may be isolated or attributed to the optical system of lithographic equipment 10 and the performance of that system may be evaluated or characterized.

With continued reference to FIG. 1, image sensor unit 102 collects, measures, senses and/or detects the aerial image produced or generated by lithographic equipment 10 in conjunction with mask 26. Image sensor unit 102 provides image data, which is representative of the aerial image, to processor/controller 104. Processor/controller 104, in response, evaluates and/or analyzes that data to inspect, characterize and/or evaluate mask 26 and/or lithographic equipment 10 (or sub-systems thereof, for example, the optical sub-system). In this regard, processor/controller 104 implements data processing and analysis algorithms to process the data from image sensor unit 102 to reconstruct a full or partial aerial image, or to extract desired information directly without reconstructing a full or partial aerial image. Such image processing may involve deconvolution or other techniques familiar to those skilled in the art.

In addition, processor/controller 104 may use the data from image sensor unit 102 to perform and evaluate critical dimension measurements, and/or conduct defect inspection, for example, by comparing the measured aerial image to a pattern design database, or perform a die-to-die inspection if there are multiple dice on the same mask. Processor/controller 104 may also implement algorithms that conduct or perform resist modeling and/or integrated circuit yield analyses.

Processor/controller 104 may be employed as a control or operator console and data/image processing device. Processor/controller 104 may store algorithms and software that process the data representative of the aerial image (received from image sensor unit 102), extract information, manage data storage, and/or interface with users/operators. Processor/controller 104 may be located near or next to lithographic equipment 10 or in another locale, which is remote from lithographic equipment 10.

It should be noted that processor/controller 104 may be a stand-alone unit, as illustrated in FIG. 1, or partially or wholly integrated in lithographic equipment 10. In this regard, suitable circuitry in lithographic equipment 10 may perform, execute and/or accomplish the functions and/or operations of processor/controller 104 (for example, evaluation and/or analysis of the data representative of the aerial image collected, measured, sensed and/or detected at the wafer plane).

Thus, in one embodiment, the inspection, characterization and/or evaluation circuitry/electronics may be partially or wholly integrated into lithographic equipment 10 and, as such, this "integrated system" may determine, assess, apply and/or implement appropriate corrective measures to enhance or improve its operation and thereby improve or enhance the quality, yield, and cost of integrated circuits manufactured therein.

It should be further noted that processor/controller 104 may also be partially or wholly integrated in, or on, image sensor unit 102. In this regard, some or all of the functions and operations to be performed by processor/controller 104 may be performed, executed and/or accomplished by suitable circuitry in, or on image sensor unit 102. As such, the collection and analysis of data representative of the aerial image may be less cumbersome in that a bus may be integrated and/or fabricated on or within image sensor unit 102 to facilitate communication of data and commands to/from the circuitry used to measure, detect and/or sense the aerial image and the circuitry used to evaluate and/or analyze the data representative of the aerial image.

With reference to FIG. 2, in one embodiment of the invention disclosed in the U.S. Pat. No. 6,828,542, an image sensor element array 106 of image sensor unit 102 is shown. Image sensor element array 106 includes a plurality of sensor elements 200, including $200a_x$ to $200h_x$ (x=1 to 8), that measure, sense, detect and/or collect incident energy or radiation.

In those instances where the dimensions of the active areas of sensor elements 200 are too large to provide a desired or required spatial resolution, it may be necessary to limit, restrict, and/or reduce these sensor cells' active areas that are exposed. Hence, image sensor element array 106 may include a patterned opaque film 204 that impedes, obstructs, absorbs, and/or blocks passage of photons or light of a given wavelength (that is, at the wavelength to be measured, sensed or detected by sensor elements 200). Opaque film 204 includes apertures 206, including $206a_x$ to $206h_x$ (x=1 to 8), so that active areas of sensor elements 200 are exposed only at apertures 206. As such, the spatial resolution of the energy measured by sensor elements 200 is enhanced or improved because the portion or area of each sensor element that is effectively exposed to and/or measures, senses, detects, and/or collects energy or radiation is limited or restricted.

Traditionally, the sampling plan and sensitivity in the prior art monitoring system for the wafer manufacturing process described above has not been informed by the known location of hot spots in the design or weak areas due to a combination of the design and the mask-making process. Wafer level metrology is limited to as few as 5 to 10 points within the field in a production process, or at most a few hundred points during initial mask qualification. Such limited samples are inadequate to fully sample the range of hot spots that might impact yield. Wafer inspection for pattern defects is even more limited than mask inspection due to the reduced signal to noise and image contrast of the resist patterns on the wafer as imaged by the wafer inspection tools. Some implementations have described a means of varying process conditions on the wafer to detect regions with locally limited process windows, but these methods are not informed by the map of expected hot spot locations, and are only sensitive to relatively large CD variations on the order of tens of nanometers. They are unable to discern CD variations on the order of 1 nm that may appear to be patterned correctly (no gross failure of the pattern) but will have a negative impact on device yield.

What is needed is a system to collect very high resolution metrology data (on the order of 1 nm sensitivity to CD variation) from a sample of thousands to millions of suspect hot spot locations across a range of process conditions and to ensure that this large number of locations is representative of all expected types of hot spots for the design and that they are distributed across the full spatial extent of the mask. Only by measuring the full effect of both mask-making variations and variation in the wafer imaging process can the full impact of the marginal design regions be accurately characterized and the process adjusted appropriately to optimize device performance and yield.

SUMMARY

A method to identify, classify, and prioritize hot spots (regions or patterns on a semiconductor wafer that tend to produce yield-limiting defects due to process variations and/or other factor) in a semiconductor design allows the identification of weak patterns within each design layer, the accurate determination of the impact of process drifts upon the patterning performance of the real mask in a real scanner, and the optimum process correction, process monitoring, and resolution enhancement technology (RET) improvements to optimize integrated circuit device performance and yield. An advantage of the present invention is the combination of high speed simulation coupled with massive data collection capability on actual aerial images and/or resist images at the specific patterns of interest provides a complete methodology for optimum RET implementation and process monitoring.

A method according to the invention comprises simulating a lithography process for a mask to produce a simulated image, identifying areas in the mask having features with a potential to fail in the simulated image, categorizing the areas in the mask having features with a potential to fail into groups, prioritizing the groups of areas in the mask having features with a potential to fail, implementing a sampling plan for obtaining data about the prioritized groups of areas in the mask having features with a potential to fail, and analyzing the data to determine which areas in the mask having features with a potential to fail should be changed in order to increase production yield. Simulating the lithography process may optionally include use of a resist model, a mask-making model, or both.

DETAILED DESCRIPTION OF THE INVENTION

A method to identify, classify, and prioritize hot spots in an integrated circuit design employs an implementation of a metrology system based upon aerial image inspection of the mask to monitor a statistical sampling of the hot spots. The method also employs the analysis of the sampled data that assists in determining whether the mask, as exposed on the scanner, can produce device wafers with acceptable yield and, if not, in modifying the process in such a way as to correct for the expected hot spot failures and to improve the device yield to an acceptable level. In addition, the method employs a simulation-based system to generate a map of potential hot spot regions. This simulation-based system may be based upon the prior art system of U.S. Pat. No. 7,003,758, or it may use any similar simulation-based approach or a rule-checking approach to produce a list of potential hot spot regions. Furthermore, the method employs aerial image inspection of the mask as exposed in a scanner. One embodiment of acquiring such aerial images employs an image sensor unit as described in previous patents such as U.S. Pat. No. 6,828,542, "System and Method for Lithography Process Monitoring and Control" and other patents based on the wafer sensor technology described therein. Other systems or methods of aerial image inspection may also be employed. Resist-based monitoring is also possible by employing either optical or e-beam based inspection or metrology tools to survey a subset of the suspect hot spot locations.

Figure 3:
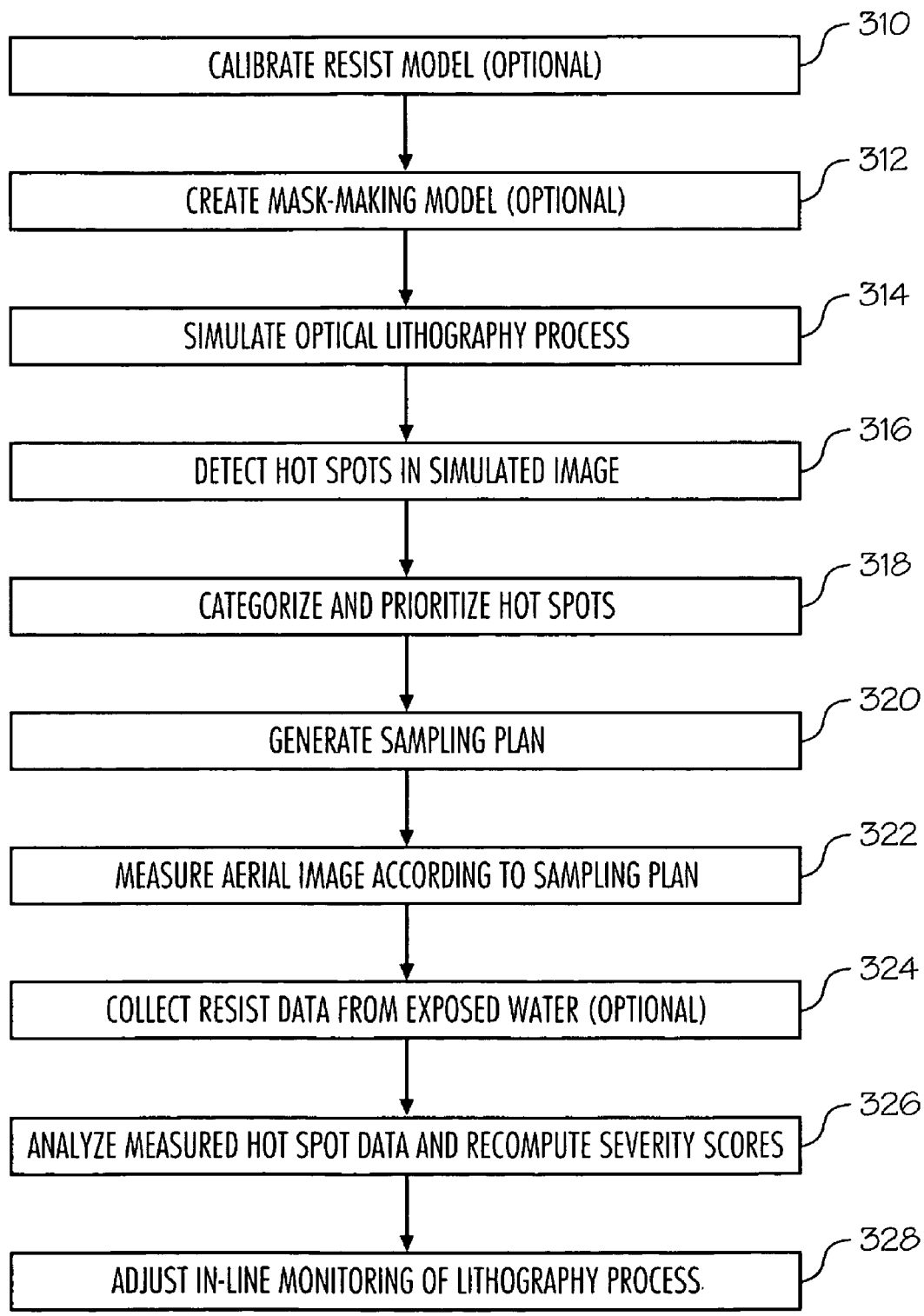
FIG. 3 is a flowchart of method steps for detecting, sampling, and analyzing hot spots in a mask, according to one embodiment of the invention.

FIG. 3 is a flowchart of method steps for detecting, sampling, and analyzing hot spots in a mask, according to one embodiment of the invention, including optional steps. In optional step 310, a resist model is calibrated. The calibrated resist model may be used during simulation step 314, described below. Resist model calibration methods are well described in the literature and can vary from simple CD vs. pitch data to complex two-dimensional test cells that are chosen to be representative of the range of features expected in the design. The test structures may include features with and without OPC correction, assist features, and phase shift structures, and the data collected for calibration purposes may include one-dimensional CD data, two-dimensional metrics of corner rounding or other geometrical parameters, three-dimensional descriptions of the full resist profile, or image based metrics such as fitting a complex outline to the edges of a full two-dimensional image. Resist models can vary from simple threshold plus bias models to more detailed image diffusion models through the resist up to and including full first principles models of the physical and chemical processes that take place in the resist layer during the exposure, bake, and develop steps. The implementation of step 310 that will be used in step 314 is not restricted to any particular calibration data set or resist model.

In optional step 312, a mask-making model is created. In step 314 described below, a simulation of the lithography process predicts how a full chip design will be patterned onto device wafers. The simulation in step 314 may assume that the pattern on the physical mask will be exactly as drawn by the designer with the addition of RET features exactly as drawn by the implementation software. This assumption is never fully valid and will result in slight inaccuracies in the predicted wafer level images and dimensions. The simulation can be improved by using a mask-making model, created in step 312, that predicts a more realistic description of how the design pattern will actually appear on the mask. Such a mask-making model can be created from historical data, from measurements of test structures or representative images of the actual device mask, from first principles models of the mask-making process, from optical images collected during the mask inspection process, or from any combination of the above methods. The method shown in FIG. 3 may benefit from the inclusion of a mask-making model in the simulation in step 314. Note that such inclusion is not restricted to any particular metrology data set or mask-making model.

In step 314, an optical lithography process is simulated. In this step, the full chip design is processed by a simulation program to find areas of potential process marginality. Some methods of performing this simulation have been described in U.S. Pat. No. 7,003,758 referenced above. The simulation in step 314 may include use of the resist model calibrated in optional step 310 and/or the mask-making model created in optional step 312.

The simulation in step 314 may be performed at only a single focus and exposure setting, at multiple focus and exposure settings, or with varying wafer and/or mask process parameters. Examples of wafer process conditions that may be varied include, but are not limited to, illumination and objective lens parameters, aberrations, vibration effects due to the scanning system, and other image degrading parameters that are well known in the art. Examples of wafer process conditions that may be varied include, but are not limited to, the nominal mask CD (mean to target offset), the selective bias of feature size vs. pitch, the corner rounding and/or line end pullback, and other systematic and random mask patterning variations that are well known in the art.

The simulation in step 314 may also include other processes in addition to the exposure process of a lithography system, such as an etch processing, metal deposition, chemical-mechanical polishing (CMP), and other processes to predict the final physical characteristics of the devices on the wafer.

The simulation in step 314 may also take into account multiple exposures at a single process layer of interest, such as double expose phase shift masks, where one mask pattern defines a regular array of fine patterns while the second pattern acts as a trim mask to define un-patterned areas or regions with larger resist features, or double dipole exposures, where one pattern is exposed with a given illumination profile optimized to print horizontally oriented features while the second pattern is exposed with a different illumination profile optimized to print vertically oriented features.

The simulation in step 314 may also take into account multiple exposures of multiple different process layers to simulate the overlay between critical structures, such as contact-to-polysilicon or via-to-metal overlay.

The output of step 314 may include, but is not limited to, the full two-dimensional outlines for some or all features in the design, three-dimensional metrics of the expected resist profiles for some or all features in the design, lists of one- and/or two-dimensional CD values at some or all positions in the design, or any combination of the above. The output of the simulation in step 314 may also include, but is not limited to, simulated aerial images at some or all locations in the design, including the potential use of a full aerial image intensity map across the entire mask area and/or a map of the aerial image slope or NILS across the entire mask area.

In step 316, hot spots in the simulated image are detected. Once the simulation in step 314 is complete, potential weak points, i.e., hot spots, in the design as a function of process conditions may be computed according to one or more definitions (e.g., certain rules, thresholds, or metrics). Hot spots may be determined based on absolute CD values, on the rate of change of CD vs. one or more of the parameters that were varied in the simulation ("CD sensitivity"), on the slope of the aerial image intensity, or on NILS where the edge of the resist feature is expected (computed from a simple threshold/bias model or a more complete resist model). Alternatively, hot spots may be determined based on a set of predetermined rules such as those used in a design rule checking system, including, but not limited to, line-end pullback, corner rounding, proximity to neighboring features, pattern necking or pinching, and other metrics of pattern deformation relative to the desired pattern. The CD sensitivity to small changes in mask CD is a particularly important lithographic parameter known as MEF (Mask Error Factor) or MEEF (Mask Error Enhancement Factor). Computation of MEF vs. focus and exposure provides a critical metric of the probability that mask process variation convolved with wafer process variation will result in unacceptable pattern degradation of a particular pattern element. Hot spots can also be identified based on variation in overlay errors relative to underlying or subsequent process layers and CD variation or by sensitivity to variations in overlay and/or CD between exposures in a multiple-exposure process.

Metrics of hot spot severity can be computed for each hot spot depending on which detection method was used to find the specific weak area. These metrics can consist of one or more of the following parameters: the magnitude of the CD variation relative to the target value, the magnitude of the CD sensitivity parameter for one or more variable input parameters (especially the MEF as a function of focus and exposure), the value of the NILS or image slope at the resist threshold relative to the value for a well patterned structure, and/or the extent to which the predetermined rule was violated for a specific pattern element.

In step 318, the detected hot spots are categorized and prioritized. The number of hot spots detected by the simulation system will always exceed the number that can reasonably be measured by any metrology tool. The number of hot spots can be reduced to a manageable number by lowering the sensitivity of the hot spot detectors in the simulation, but this leads to an unacceptable high risk of missing a key defect. This tradeoff is inherent in the nature of hot spots. They are not outright failures or defects but rather points where the process might fail as a function of the normal range of variations in the mask and wafer processes. The number of hot spots that needs to be reviewed can be reduced to a manageable number by grouping them into categories of similar patterns and by prioritizing the categories based on severity.

Categorizing the hot spots into groups can be accomplished in several ways. At the highest level, the hierarchy of the design data may be applied to identify design regions that are nominally identical. The hierarchy breaks down quickly with the use of aggressive RET since patterns that are exactly identical as initially drawn can be modified in very different ways due to subtle differences in the local neighborhood of the features within the full design. Categorizing the hot spots into groups can also be accomplished by comparing the simulated aerial or resist images and then collecting patterns that are substantially the same into a common group. The degree to which two or more patterns must agree to be considered the same can be preset based on simulated CDs or aerial image values. Matching parameters can also be modified based on pattern specific parameters such as CD and pitch. Also, the parameters of smaller features may be required to match more closely than those of larger features.

Designer intent may also be an input as a factor in categorizing the hot spots. Features marked by the designer or by the automated layout software as being more critical can be required to match more closely than less critical features. The use of designer intent in hot spot detection and dispositioning is well known in the art and hence will not be fully described here. As one example, designer intent may be applied to require tighter pattern matching in active transistor regions (areas in which a polysilicon gate overlaps active source/drain patterns on underlying layers), where polysilicon gate CD variation is most critical, as opposed to non-active regions (areas in which the polysilicon overlaps isolation areas on the underlying layer). The least restrictive matching criteria may be applied to dummy gates or CMP dummy fill regions. Designers may also flag particular features that are known to be most critical to the electrical performance of the device.

Categorizing the hot spots into groups can also be accomplished based on the nature of the hot spots detected during step 316, such as by comparing the design rule, CD limit, or sensitivity parameter violation that resulted in the identification of a specific feature as a weak point. Features that are substantially similar in geometry and detection conditions may be preferentially grouped together. In addition, the response of the suspected hot spots as a function of process window conditions can be used as a factor in grouping, i.e., hot spots that have nearly identical responses to changes in focus and exposure, or other process conditions will be grouped together. Such process-condition based grouping can also be performed for hot spots that differ in pattern sizes or shapes but respond in a nearly identical manner to changes in the process conditions, thereby allowing the prioritization of those hot spots that have the most critical sensitivity to drifts in process conditions and postponing efforts to repair hot spots that only occur at the least likely settings of the process conditions.

Each group of hot spots can be prioritized based on a combination of parameters, including, but not limited to, the metrics of hot spot severity discussed above, the number of substantially identical hot spots detected in each category, and the likelihood that the variation in the particular pattern or geometry will result in device failure. The computation can be based on designer intent, on automated geometrical arguments regarding both the process layer being analyzed as well as the layers above and below, on pattern dependent rules based on which patterns are known to be most lithographically sensitive to process variation, or on combinations of the above. For example, patterns that are electrically connected to critical circuit elements will have higher priority than those that are not. Patterns that are supposed to have the smallest CDs at the most difficult pitches to pattern (near the so-called "forbidden pitches") will be prioritized above larger CDs, or similar CDs at less lithographically demanding pitches, and so on. These prioritization rules may be based on known inputs from lithography experience, or they may be computed on the fly based on the NILS and aerial image intensity and contrast of the pattern. This list of different means of prioritization is not intended to be exhaustive and may be applied in any combination with the rules for categorization.

In step 320, a sampling plan is generated. After the hot spots have been categorized and prioritized, a sample plan can be developed to optimize the collection of the maximum amount of information about the hot spots in the minimum possible time. The sampling plan should be optimized to ensure that the most critical hot spot groups are inspected at as many points as possible across the mask in order to measure the effects of the critical hot spot groups convolved with the mask-making process and the scanner lens aberrations as a function of its position in the lens field. The sampling plan should also ensure that as many hot spot groups as possible are measured at least once, with higher priority being allocated to the more critical hot spots. A tradeoff between the number of samples of each hot spot group vs. the number of hot spot groups measured can be determined, with a weighting factor applied to each group of hot spot based on the severity assigned to that group. Multiple sampling plans that are different can be considered for a given number of measurements allocated among the different groups of hot spots. The sampling plan with the highest computed score is then selected as the optimum sampling plan.

Figure 1:
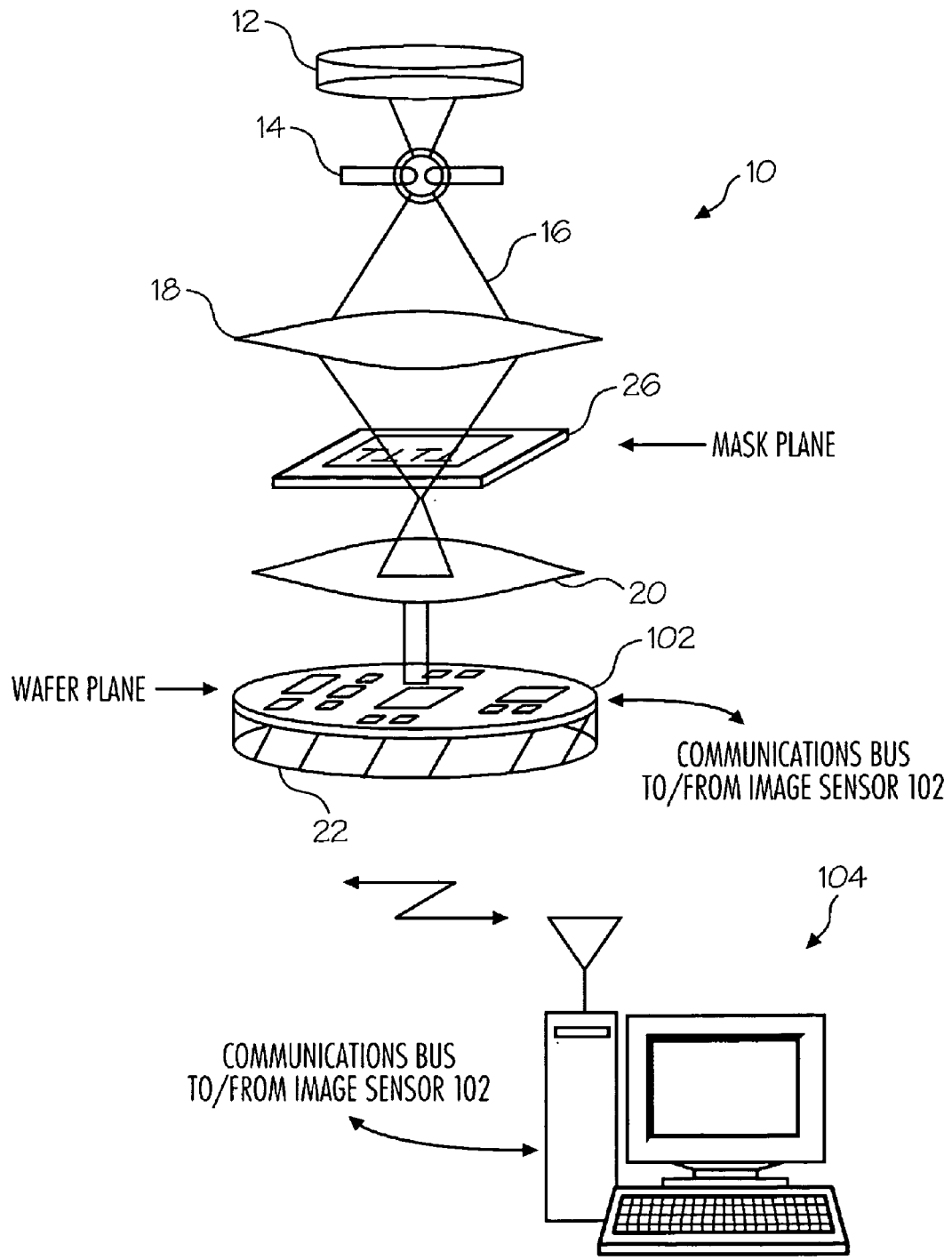
FIG. 1 is a block diagram of a prior art aerial image sensing system.
Figure 2:
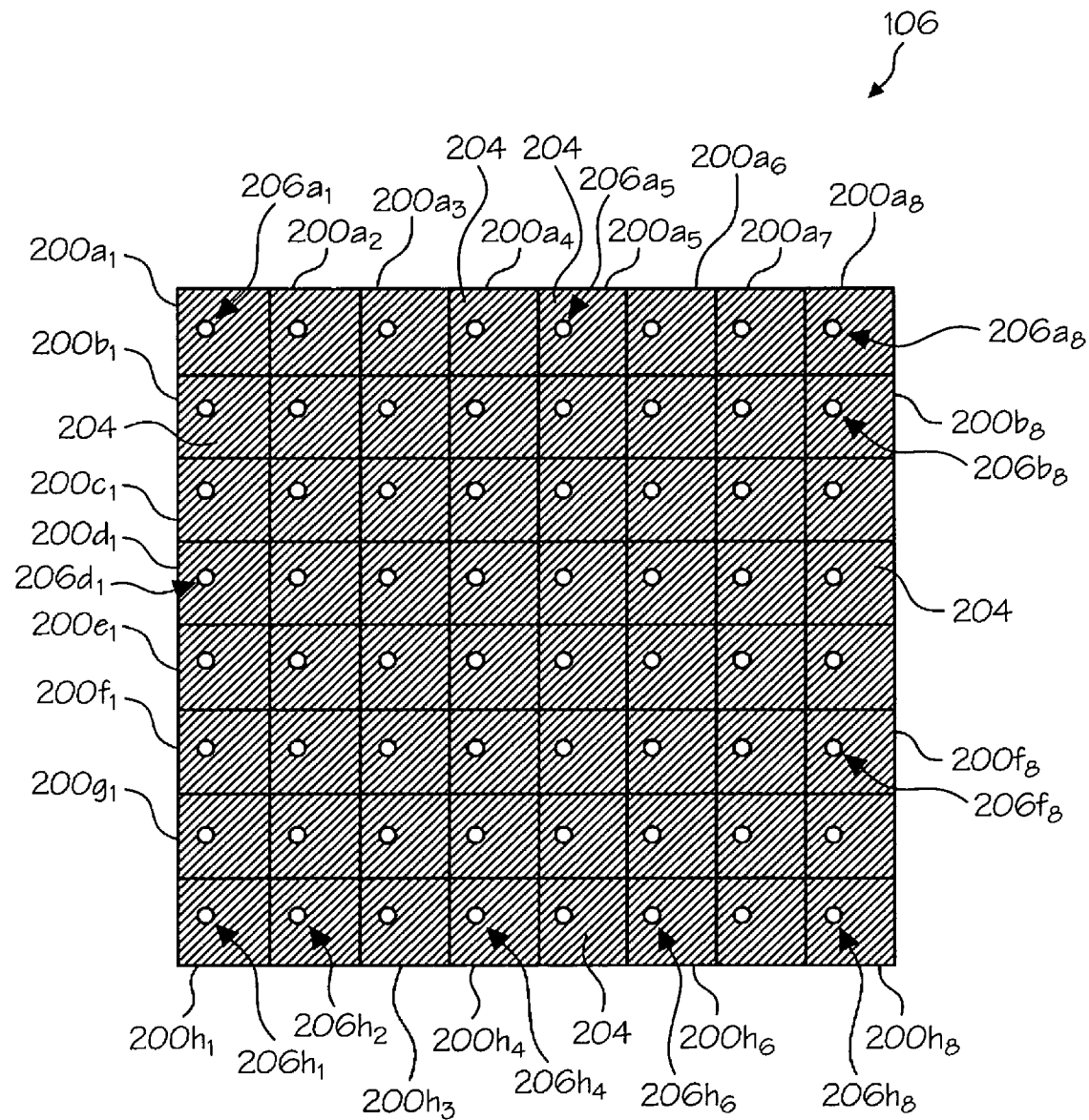
FIG. 2 is a two-dimensional (top view) schematic representation of a prior art image sensor element array, in conjunction with a selectively patterned, shaped, and/or etched opaque film.

As described below, one method of aerial image data collection that can be used during step 322 of the method of FIG. 3 uses a previously patented image sensor unit described in U.S. Pat. Nos. 6,828,542, 6,806,456, and 6,803,554, the subject matters of which are incorporated herein by reference in their entirety, to collect millions of data points simultaneously. The advantage is that the volume of data available with image sensor unit 102 (as shown in FIG. 1) exceeds the volume that can be collected with conventional tools by orders of magnitude. The disadvantage is that image sensor unit 102 must be placed in an exposure tool to collect the data, preventing the tool from being used to produce products while data collection is in progress. One full set of images (one aerial image approximately 1 micron on a side) can be collected in roughly ten minutes. Idling a production scanner that costs $10-$20M for this short time in return for improved process performance is commonly seen as a desired tradeoff.

Image sensor unit 102 collects data using an array 106 of image sensor elements 200, typically arranged in a regular grid like layout as part of a CCD detector. As a result, the millions of images collected by image sensor elements 200 are likewise arranged in a regular grid separated by the sensor-element-to-sensor-element repeat distance of the array (typically a value between 5 and 10 microns). Since the hot spots are not usually found on a regular gridded layout with the same unit cell as the sensor array 106, only a fraction of the hot spots are likely to be imaged in one exposure of image sensor unit 102. If the unit cell is a 5-micron-by-5-micron array, and the images are 1 micron on a side, a single exposure in the scanner will image about 4% of the area of the mask. If the unit cell of the sensor is 10 microns on a side, then the sampled area drops to 1% of the mask.

Assuming that the potential hot spots are distributed randomly across the exposure field of the exposure tool, it is reasonable to assume that the percentage of hot spot candidates that would be collected in a single exposure of image sensor unit 102 is approximately the same as the percentage of the mask area sampled in a single exposure, or between 1% and 4% for the currently available sensor elements. Given the very high number of candidate hot spots (on the order of millions), a single exposure would be expected to sample on the order of hundreds of thousands of hot spots. While it is only a small percentage of the total number of candidate hot spots, it is many orders of magnitude more than the number that could be reasonably measured in a conventional metrology tool such as a CD-SEM. A sampling plan can be determined as described above to optimize data collection for the most severe types of hot spot candidates, with the added constraint that they must lie near (within roughly one half of the individual image size) the vertices of a grid with the same repeat distance as image sensor element array 106. A high speed computer can compute the optimum positioning of image sensor element array 106 relative to the mask field to maximize the sampling plan score. Image sensor element array 106 can be offset in x and y and rotated by an angle $\theta$ to fit the points imaged by image sensor element array 106 to the maximum number of high value hot spots. (The angle $\theta$ may be limited by the range of motion of the exposure tool stage). The size of the images may also be varied to capture more candidate hot spot locations at the cost of more scanner time to expose the images. This tradeoff can be calculated by the computer and reported to the user to present alternative sampling plans that trade more exposure tool time for higher sampling plan scores. Sampling plans using more than one imaging exposure can also be computed, and a range of options of total sampling score vs. exposure tool time can be presented to the user for selection.

In step 322, the aerial image is measured according to the sampling plan. Data is collected according to the optimum sampling plan described above in step 320. In one embodiment, image sensor unit 102 is loaded into the scanner and offset in x, y and $\theta$ according to the optimum sampling plan to collect as many high value images as possible in one or more imaging exposures, thereby collecting the largest possible data set in the shortest possible time. Minimizing the time that the scanner must be used is a primary consideration of this approach. Image sensor unit 102 can collect through focus aerial image information as an integral part of the data collection. The through focus data can be analyzed on an offline computer such as the one used in the simulation system to simulate the expected aerial image and/or resist performance as a function of both focus and exposure, thereby fully mapping the process window for each hot spot measured by image sensor unit 102.

The aerial image data may be collected on more than one exposure tool in the semiconductor manufacturing facility in order to determine which exposure tool will have the best pattern performance for the given mask being tested. The data may also be collected at different times over a period of hours, days, or weeks in order to track the stability of the exposure system for the particular mask being tested.

In optional step 324, resist data from an exposed wafer is collected. The aerial image data collected by image sensor unit 102 may be supplemented by resist image data. In this optional step, wafers would be exposed either at fixed focus and exposure, as an array of shots with different focus and exposure settings across the wafer (FEM, focus exposure matrix), or as an array of shots where either focus or exposure is varied across the wafer. CD data from these wafers can be collected using any standard CD metrology tool, such as an SEM or an optical CD measuring tool. The resist data may be compared to the aerial image data and simulated resist results, and any differences between the CD values predicted by the image sensor unit 102 and/or simulation system may be used to fine-tune the models used for computing CDs from the measurements by image sensor unit 102 and applied to all of the data collected with image sensor unit 102, thereby providing more accurate CD results from the many hot spot locations imaged by image sensor unit 102. Only a limited subset of the locations measured by image sensor unit 102 needs to be verified by the independent resist measurements in order to improve the accuracy of all of the data collected by image sensor unit 102.

In step 326, the measured hot spot data is analyzed and the severity scores are recomputed. Once data is collected for the optimal set of candidate hot spots according to the sampling plan, an analysis can determine which hot spots will have the biggest impact on the available process window. The severity of each hot spot can be recomputed as in the categorization step 318 described above, but here in step 326 the hot spots are ranked based on actual observed impact on CD performance instead of simulated results. Unlike the simulated data, the new severity scores account for the impact of the actual physical mask as well as for the actual patterning performance of the real scanner. These new values therefore provide a much more accurate metric of the impact of the hot spots upon expected device performance and yield. The new scores can be used in a wide variety of ways, some but not all of which are listed below:

Determination of the best operating conditions for product exposures;

Determination of which exposure tool in the semiconductor manufacturing facility will give the best results for a specific mask;

Determination of the acceptability (pass/fail) of a specific mask for production;

Determination of which points in the exposure field of the tool should be measured by routine in-line production monitoring (CD and/or overlay) for statistical process control (SPC) and/or advanced process control (APC) based process control for the earliest possible detection of process deviations which may result in unacceptable device failures;

Determination of which points in the exposure field should be routinely monitored by optical or electron beam based in-line defect monitoring and review tools for the earliest possible detection of process deviations that may result in unacceptable device failures;

Determination of which specific devices and which layers within those devices that need to be studied in more detail for determining if changes must be made in the wafer and/or mask process and/or RET implementation to produce more manufacturable designs with greater tolerance to normal process variations;

Recomputation of the expected electrical performance of the circuit being produced to determine how it will perform based on the actual printed pattern at the wafer level instead of the idealized performance usually calculated based on the assumption of perfect pattern replication; and Adjustment of the process, design rules, and/or RET implementation rules to deliver improved CD performance and electrical performance of the device and to improve the RET implementation for future designs.

In step 328, in-line monitoring of the lithography process is adjusted. Based on the analysis results of step 326, the in-line monitoring plans for CD, overlay, and/or defects may be adjusted to provide optimum sensitivity at the weakest points in the design in order to detect any unacceptable process drift or pattern degradation at the earliest possible point. This early detection of pattern specific yield-limiting process drifts can greatly improve the manufacturability and yield of a given product. The improved sampling plans will be more sensitive to process drifts that affect the yield-limiting patterns than current in-line monitors that measure scribe-line test structures or points within the device that may not have the highest targeted sensitivity to yield-limiting process drifts. The improved sampling plans may also specify the frequency at which metrology and inspection should be performed, based on the severity scores and CD sensitivities determined for the most critical hot spots. The computed maps of hot spot distribution and impact on CD across the field may also be used to optimize the metrology and/or defect inspection recipes to provide optimum sensitivity to the most probable types of pattern failures predicted from the measured hot spot results. Preventive maintenance and routine monitoring of the process tools, such as the exposure, etch, or CMP tools, can also be modified based on these results to more carefully check and repair the specific process drifts that have the largest impact on the fidelity and CD performance of the weakest points in the design, for example, specific scanner lens aberrations or CMP or etch non-uniformity vs. CD and pitch.

A library of hot spot groups with their associated severity scores may be created and maintained by the user. Such a library may be analyzed to determine hot spots on different masks that are substantially similar in terms of appearance, geometry, and impact on the process window, among other parameters. Hot spots that are similar enough may be grouped together between different masks, just as the candidate hot spots for a single mask were categorized above, and a new severity score may be assigned to each new group based on how often the hot spot appears on multiple masks, not just on a single mask. In-line metrology and defect monitoring in the manufacturing facility may be adjusted to be more sensitive to the most frequently occurring or most sever hot spots that affect multiple designs. If an unacceptable CD variation or pattern degradation is found in production for any mask, the library can be searched (manually or automatically) to determine which other masks and designs may experience a similar unacceptable loss of pattern fidelity, and additional monitors or process corrections may be applied to all designs with substantially the same weak pattern to ensure that they do not suffer any performance or yield loss due to the failure of the pattern in question.

What is claimed is:

1. A method for analyzing areas in a mask having features with a potential to fail, comprising:
   simulating a lithography process to produce a simulated image corresponding to the mask;
   analyzing the simulated image to identify areas in the mask having features with a potential to fail in the simulated image;
   categorizing the areas in the mask having features with a potential to fail into groups of similar patterns;
   prioritizing the groups of areas in the mask having features with a potential to fail based on severity;
   creating a sampling plan for obtaining data about the prioritized groups of areas in the mask having features with a potential to fail by applying a weighting factor to each prioritized group based on a priority assigned to that group;
   generating an aerial image using the mask using a single setting of the lithographic process; and
   inspecting portions of the aerial image corresponding to one or more of the identified areas from the simulated image according to the sampling plan.

2. The method of claim 1, further comprising:
   determining and calibrating a resist model to capture resist offsets; and
   using the resist model while simulating the lithography process.

3. The method of claim 1, further comprising:
   creating a mask-making model; and
   using the mask-making model while simulating the lithography process.

4. The method of claim 1, further comprising:
   exposing a wafer using the mask having features with a potential to fail; and
   collecting resist data from the exposed wafer.

5. The method of claim 1, further comprising:
   determining and calibrating a resist model to capture resist effects;
   creating a mask-making model; and
   using the resist model and the mask-making model while simulating the lithography process.

6. The method of claim 1, wherein inspecting an aerial image of the mask according to the sampling plan includes measuring the intensity of an aerial image projected onto an image sensor unit configured to be placed in a wafer stage of an exposure tool.

7. The method of claim 1, wherein analyzing the simulated image includes determining critical dimension values of the features having a potential to fail from the simulated image.

8. A method for analyzing areas in a mask having features with a potential to result in low production yield, comprising:
   simulating a lithography process to produce a simulated image corresponding to the mask;

analyzing the simulated image to identify areas in the mask having features with a potential to result in low production yield in the simulated image;

grouping the areas in the mask having features with a potential to result in low production yield into groups of similar patterns;

prioritizing the groups of areas in the mask having features with a potential to result in low production yield according to metrics of severity;

creating a sampling plan for obtaining data about the prioritized groups of areas in the mask having features with a potential to result in low production yield by applying a weighting factor to each prioritized group based on a priority assigned to that group;

generating an aerial image using the mask using a single setting of the lithographic process; and inspecting portions of the aerial image corresponding to one or more of the identified areas from the simulated image according to the sampling plan.

9. The method of claim 8, further comprising:
determining and calibrating a resist model to capture resist effects; and
using the resist model while simulating the lithography process.

10. The method of claim 8, further comprising:
creating a mask-making model; and
using the mask-making model while simulating the lithography process.

11. The method of claim 8, further comprising:
exposing a wafer using the mask having features with a potential to fail; and
collecting resist data from the exposed wafer.

12. The method of claim 8, further comprising:
determining and calibrating a resist model to capture resist effects;
creating a mask-making model; and
using the resist model and the mask-making model while simulating the lithography process.

13. The method of claim 8, wherein inspecting an aerial image of the mask according to the sampling plan includes measuring the intensity of an aerial image projected onto an image sensor unit configured to be placed in a wafer stage of an exposure tool.

14. The method of claim 8, wherein analyzing the simulated image includes determining critical dimension values of the features having a potential to result in low production yield from the simulated image.

15. A method for analyzing areas in a mask, comprising:
simulating a lithography process to produce a simulated image corresponding to the mask;
analyzing the simulated image to detect areas in the mask having features with a small process window in the simulated image;
categorizing the areas in the mask having features with a small process window into groups based upon predetermined critical features;
prioritizing the groups of areas in the mask having features with a small process window based on severity;
creating a sampling plan for obtaining data about the prioritized groups of areas in the mask having features with a small process window by applying a weighting factor to each prioritized group based on a priority assigned to that group;
generating an aerial image using the mask using a single setting of the lithographic process; and
inspecting portions of the aerial image corresponding to one or more of the identified areas from the simulated image according to the sampling plan.

16. The method of claim 15, further comprising:
determining and calibrating a resist model to capture resist effects; and
using the resist model while simulating the lithography process.

17. The method of claim 15, further comprising:
creating a mask-making model; and
using the mask-making model while simulating the lithography process.

18. The method of claim 15, further comprising:
exposing a wafer using the mask having features with a potential to fail; and
collecting resist data from the exposed wafer.

19. The method of claim 15, further comprising:
determining and calibrating a resist model to capture resist effects;
creating a mask-making model; and
using the resist model and the mask-making model while simulating the lithography process.

20. The method of claim 15, wherein inspecting an aerial image of the mask according to the sampling plan includes measuring the intensity of an aerial image projected onto an image sensor unit configured to be placed in a wafer stage of an exposure tool.

21. The method of claim 15, wherein analyzing the simulated image includes determining critical dimension values of the features having a small process window from the simulated image.

22. A method for analyzing areas in a mask having features with a potential to fail, comprising:
analyzing a simulated aerial image corresponding to the mask to identify areas in the mask having features with a potential to fail in the simulated aerial image;
categorizing the areas in the mask having features with a potential to fail into groups of similar patterns;
prioritizing the groups of areas in the mask having features with a potential to fail based on severity;
creating a sampling plan for obtaining data about the prioritized groups of areas in the mask having features with a potential to fail by applying a weighting factor to each prioritized group based on a priority assigned to that group;
generating an aerial image using the mask using a single setting of a lithographic process corresponding to the simulated aerial image; and
inspecting portions of the aerial image corresponding to one or more of the identified areas from the simulated aerial image according to the sampling plan such that more data is obtained for high-priority groups than for low-priority groups.

23. The method of claim 22, further comprising:
determining and calibrating a resist model to capture resist effects; and
using the resist model while simulating the lithography process.

24. The method of claim 22, further comprising:
creating a mask-making model; and
using the mask-making model while simulating the lithography process.

25. The method of claim 22, further comprising:
exposing a wafer using the mask having features with a potential to fail; and
collecting resist data from the exposed wafer.

26. The method of claim 22, further comprising:
determining and calibrating a resist model to capture resist effects;
creating a mask-making model; and
using the resist model and the mask-making model while simulating the lithography process.

27. The method of claim 22, wherein inspecting an aerial image of the mask according to the sampling plan includes measuring the intensity of an aerial image projected onto an image sensor unit configured to be placed in a wafer stage of an exposure tool.

28. The method of claim 22, wherein analyzing the simulated aerial image includes determining critical dimension values of the features having a potential to fail from the simulated aerial image.

* * * * *